United States Patent [19]

Roberts et al.

[11] Patent Number: 5,418,201

[45] Date of Patent: May 23, 1995

[54] HYDROGENATION CATALYST AND PROCESS FOR PREPARING SAME

[75] Inventors: Brian D. Roberts, Cleveland Heights; Deepak S. Thakur, Solon; Thomas J. Sullivan, Strongsville; Robert A. Plundo, Hudson, all of Ohio

[73] Assignee: Engelhard Corporation, Iselin, N.J.

[21] Appl. No.: 77,216

[22] Filed: Jun. 15, 1993

Related U.S. Application Data

[62] Division of Ser. No. 874,259, Apr. 24, 1992, Pat. No. 5,243,095.

[51] Int. Cl.⁶ .......... B01J 23/84; B01J 23/34; B01J 21/04; B01J 37/03
[52] U.S. Cl. .......... 502/245; 502/324
[58] Field of Search .......... 502/324, 245

[56] References Cited

U.S. PATENT DOCUMENTS

| | | | |
|---|---|---|---|
| 2,127,367 | 8/1938 | Normann | 568/877 X |
| 2,569,671 | 10/1948 | Hughes | 568/914 |
| 2,725,400 | 11/1955 | Mecorney et al. | 502/324 X |
| 3,271,324 | 9/1966 | Stephens et al. | 502/331 |
| 3,759,825 | 9/1973 | Chun et al. | 502/245 X |
| 3,759,845 | 9/1973 | Rudoff et al. | 502/245 |
| 3,789,020 | 1/1974 | Carter et al. | 502/245 X |
| 3,799,887 | 3/1974 | Brennan et al. | 502/324 X |
| 3,853,922 | 12/1974 | Yamaguchi et al. | 502/324 X |
| 3,925,490 | 12/1975 | Reich et al. | 502/244 X |
| 3,974,102 | 8/1976 | Kaiser | 502/330 |
| 3,991,127 | 11/1976 | Corr et al. | 502/245 X |
| 4,144,198 | 3/1979 | Miya et al. | 502/331 |
| 4,252,689 | 2/1981 | Miya | 502/331 |
| 4,278,567 | 7/1981 | Miya | 502/331 |
| 4,443,639 | 4/1984 | Pesa et al. | 568/885 |
| 4,551,444 | 11/1985 | Ling et al. | 502/324 X |
| 4,562,174 | 12/1985 | Stiles | 502/324 X |
| 4,605,639 | 8/1986 | Dyer et al. | 502/331 |
| 4,657,888 | 4/1987 | Mesters et al. | 502/331 |
| 4,665,042 | 5/1987 | Budge | 502/61 |
| 4,748,144 | 5/1988 | Monnier | 502/331 X |
| 4,977,123 | 12/1990 | Flytzani | 502/331 X |
| 5,004,844 | 4/1991 | Van Leeuwen et al. | 568/880 |
| 5,030,771 | 7/1991 | Fuhrmann et al. | 568/814 |
| 5,043,485 | 8/1991 | Fleckenstein et al. | 502/241 X |
| 5,134,108 | 7/1992 | Thakur et al. | 502/324 X |

FOREIGN PATENT DOCUMENTS

| | | |
|---|---|---|
| 0320074 | 6/1989 | European Pat. Off. |
| 3008988 | 10/1980 | Germany |
| 4028295 | 3/1992 | Germany |
| 1200730 | 7/1970 | United Kingdom |
| 2045106 | 10/1980 | United Kingdom |
| 762964 | 5/1978 | U.S.S.R. |

OTHER PUBLICATIONS

"Hydrogenolysis of Higher Fatty Ester to Higher Alcohol Using Fe-based Catalyst", Ikeda, Morioka Komori, Chemical Abstracts, vol. 69, 1968 no month available.

*Primary Examiner*—Paul Lieberman
*Assistant Examiner*—Douglas J. McGinty

[57] ABSTRACT

In one embodiment, the invention relates to a catalyst in powdered form comprising the oxides of copper, iron, aluminum and manganese wherein the atomic ratio of copper to iron is at least 1:1. In another embodiment, the invention relates to a process for preparing such hydrogenation catalysts which comprises the steps of (A) preparing a first aqueous solution containing at least one water-soluble copper salt, at least one water-soluble iron salt, and at least one water-soluble manganese salt;

(B) preparing a second solution containing at least one water-soluble basic aluminum salt and at least one alkaline precipitating agent;

(C) mixing the first and second solutions wherein an insoluble solid is formed;

(D) recovering the soluble solid; and (E) calcining the recovered solid to form the desired catalyst.

The invention also relates to a process for hydrogenating aldehydes, ketones, carboxylic acids and carboxylic acid esters.

23 Claims, No Drawings

HYDROGENATION CATALYST AND PROCESS FOR PREPARING SAME

This is a divisional of application Ser. No. 07/874,259, filed Apr. 24, 1992, now U.S. Pat. No. 5,243,095.

TECHNICAL FIELD

This invention relates to catalysts which are particularly useful as hydrogenation catalysts, and more particularly, to copper containing catalysts useful in hydrogenating aldehydes, ketones, carboxylic acids and carboxylic esters. The invention also relates to a method of preparing said catalysts and to the use of the catalysts in hydrogenation reactions.

BACKGROUND OF THE INVENTION

The preparation of various copper-containing catalysts, and the use of such catalysts in various reactions have been described previously. Such reactions include hydrogenation reactions, the synthesis of methanol and high alcohols from synthesis gas, etc. Previously known copper-containing catalysts also may contain other metal oxides including chromium oxide, zinc oxide, titanium oxide, zirconium oxide, alumina, silica, etc., and mixtures of one or more of said oxides.

The hydrogenation of carboxylic acids and carboxylic esters to alcohols is known in the art, and various methods and catalysts have been suggested for effecting the hydrogenation reaction. For example, the ester may be reduced with lithium aluminum hydride or sodium and alcohol. Another commonly practiced method involves the use of a copper-chromite-based hydrogenation catalyst. While copper chromite catalysts are commercially available and successful, the disposal of the spent copper chromite catalyst is a problem since the chromium is present in the spent catalyst. Because of stringent environmental regulations, the cost of the manufacture, use and disposal of copper chromite catalyst has increased. Thus, it is desirable to prepare copper-containing catalysts which are free of chromium.

Catalysts comprising copper, iron and a support such as alumina, and various methods of preparing such catalysts are described in a number of prior patents and publications. In one group of catalysts, iron oxide is the predominating metal oxide whereas in another group of catalysts, alumina is the predominating oxide. Catalysts wherein the copper oxide is the predominating oxide, also have been described in the prior art.

U.S. Pat. No. 4,252,689 describes a method of preparing a copper-iron-alumina catalyst by separately and simultaneously adding dropwise to a bath of water (a) an aqueous solution of cupric, ferrous and aluminum salts, and (b) an aqueous solution of an alkali metal compound effective to precipitate the copper, iron and aluminum ions, and then agitating the reaction mixture at a temperature of at least 50° C. at a pH of 9.5 to 11.5 for from 10 minutes to 10 hours. The precipitate is recovered and treated to convert it to an active catalyst. The quantitative ratio of iron and aluminum atoms each to a copper atom is indicated as being preferably from 0.4 to 2.5 and 0.4 to 2.0, respectively. The patentees indicate that if the ratio deviates from the stated ranges, the catalyst obtained has small activity, and at the same time forms many by-products when used in hydrogenation. U.S. Pat. No. 4,278,567 describes a similar process for preparing a copper-ion-aluminum catalyst wherein urea is added to the aqueous solution of the cupric salt, ferrous salt and aluminum salt, and the solution is heated prior to the addition of an alkali to form a precipitate which is treated to convert it to a catalyst.

Five-component catalyst compositions are described in U.S. Pat. No. 4,551,444, and the essential components are copper, an iron group component, a component of elements 23–26, an alkali metal compound and a precious metal compound. The catalyst may be supported on alumina or silica.

U.S. Pat. No. 4,977,123 describes extruded sorbent compositions comprising mixed oxide components of copper oxide, iron oxide and alumina, and a clay binder material. The preferred combinations disclosed in Col. 6, lines 40–44 contain 1–5 copper atoms, 0–6 iron atoms and 2–6 aluminum ions. Specific examples identified are 3 $CuO:Fe_2O_3Al_2O_3$ and $CuO:Fe_2O_3:Al_2O_3$.

European Patent Application 320,074 published Jun. 14, 1989 describes a supported catalyst which comprises a carrier material such as alumina with copper as an active component and iron as a promoter. The proportion of iron, calculated on the amount of copper and iron jointly, on an atomic basis is no more than 25%. A process is described for preparing the supported catalyst which comprises introducing ferric ions either by injection or by electrochemical generation, optionally simultaneously with cupric ions and/or a solution of a precursor of the carrier material into a third solution or suspension wherein the pH of the solution or suspension is maintained at a value of between 4 and 7 with the proviso that if a ferric solution is injected into a suspension of a carrier already containing copper, the pH of the solution does not exceed 5.9.

Soviet Union Patent 762,964, according to an English Abstract, describes a catalyst for oxidation of carbon dioxide which can be obtained from an aluminum hydroxide gel with a pseudo-boehmite structure and a moisture content of 55–85% as the base, and treating the base with the suspension of formate, acetate or oxalate of manganese, cobalt, nickel, copper or iron or their mixtures in an amount of 0.5 to 12% by weight.

Although many copper-containing catalysts have been described in the prior art, there continues to be a need to improve the characteristics and performance of such catalysts, particularly in the hydrogenation of aldehydes, acids and esters. It is also desirable to prepare catalysts which are useful in hydrogenation reactions which can be carried out in either a fixed bed or a fluidized bed reaction.

SUMMARY OF THE INVENTION

In one embodiment, the invention relates to a catalyst in powdered form comprising the oxides of copper, iron, aluminum and manganese wherein the atomic ratio of copper to iron is at least 1:1. In another embodiment, the invention relates to a process for preparing such hydrogenation catalysts which comprises the steps of (A) preparing a first aqueous solution containing at least one water-soluble copper salt, at least one water-soluble iron salt, and at least one water-soluble manganese salt;

(B) preparing a second solution containing at least one water-soluble basic aluminum salt and at least one alkaline precipitating agent;

(C) mixing the first and second solutions whereby an insoluble solid is formed;

(D) recovering the soluble solid; and (E) calcining the recovered solid to form the desired catalyst.

The invention also relates to a process for hydrogenating aldehydes, ketones, carboxylic acids and carboxylic acid esters.

DESCRIPTION OF THE PREFERRED EMBODIMENTS

In one embodiment, the present invention relates to a catalyst in powder form comprising the oxides of copper, iron, aluminum and manganese wherein the atomic ratio of copper to iron is at least 1:1. The powders have a surface area of at least about 50 m$^2$/g, and generally the powders have a surface area in the range of from about 50 or 70 up to about 150 or 160 or even 175 m$^2$/g. Those skilled in the art often refer to catalysts containing the metal oxides as the "oxide" or "oxidic precursor" form of the catalyst even though not all of the metal is in the oxide form. It should also be understood that the metals may be present in different valence states. The catalysts of the present invention generally are free of chromium.

As mentioned above, the atomic ratio of copper to iron in the catalyst of the present invention is at least 1:1. In another embodiment, the atomic ratio of copper to iron is in the range of from 3:1 or 4:1 up to about 6:1.

The amount of alumina oxide contained in the catalyst of this invention may be varied over a wide range although the atomic ratio of copper to aluminum generally is from about 1:1 to about 3:1. The catalyst of the invention generally will contain from about 1% to about 15% by weight of aluminum.

In addition to the copper, iron and aluminum, the catalysts of the present invention also contain manganese. Generally, the catalysts will contain from about 1% to about 15% by weight of manganese. In another embodiment, the catalyst contains from about 1% to about 10% by weight of manganese. The atomic ratio of copper to manganese in the catalyst may be from about 2:1 to about 35:1. The inclusion of the manganese generally improves the activity of the catalyst.

It has also been found advantageous to include a small amount of at least one porous inorganic carrier material in the catalyst, and the catalyst of the invention may contain up to about 20% by weight of the carrier. Examples of such carriers are diatomaceous earths, calcium or magnesium silicate, fiberglass and aluminas. Calcium silicate is the preferred carrier material. The inclusion of porous inorganic carrier material in the catalyst increased the ability to separate the catalyst from the product when the catalyst is used as a hydrogenation catalyst.

Various procedures can be utilized to prepare the copper catalysts of the present invention. For example, individual aqueous solutions of the salts of copper, iron, aluminum and manganese may be prepared and mixed together followed by the addition of an aqueous alkaline solution. Alternatively, a first aqueous solution comprising at least one water-soluble copper salt, at least one water-soluble iron salt and at least one water-soluble manganese salt, and a second solution comprising a water-soluble base and at least one water-soluble aluminum salt can be prepared, and these two solutions are then added simultaneously to a vessel containing water. Alternatively, a separate aqueous solution of the manganese salt can be prepared and combined with the first and second solutions. In any of the above embodiments, aqueous slurries are formed in the vessels, and the solids are recovered from the slurries. The desired catalyst is obtained by calcining the recovered solids.

One embodiment of the present invention relates to a preferred process for preparing a hydrogenation catalyst comprising the oxides of copper, iron, aluminum and manganese, and the process comprises the steps of (A) preparing a first aqueous solution containing at least one water-soluble copper salt, at least one water-soluble iron salt, and at least one water-soluble manganese salt wherein the atomic ratio of copper to iron in the first aqueous solution is at least 1:1;

(B) preparing a second solution containing at least one water-soluble basic aluminum salt and at least one alkaline precipitating agent;

(C) mixing the first and second solutions whereby an insoluble solid is formed;

(D) recovering the insoluble solid; and (E) calcining the recovered solid.

The first and second solutions described above may be mixed in any manner or order. Thus, the first solution can be added to the second solution, or the second solution can be added to the first solution, or a mixture of the two solutions can be obtained by simultaneously mixing the two solutions such as by simultaneously adding the two solutions to a vessel. Generally, the vessel to which the first and second aqueous solutions are added contains water. When it is desired to include a porous inorganic carrier in the catalyst of the invention, the carrier is included in the water contained in the vessel. For example, the vessel can contain a suspension of calcium silicate in water. Alternatively, water can be added to the vessel as the first and second aqueous solutions are simultaneously added to the vessel. It is desirable that the mixing of the first and second solutions in step (C) be conducted at a pH above about 5.5 and more generally above about 6. When the two solutions are mixed simultaneously, the pH of the resulting mixture can be controlled by varying the rate of addition of the first solution or the second solution which contains an alkaline material. As the rate of addition of the second solution increases, the pH of the resulting mixture increases. The temperature of the aqueous solutions and the slurry contained in the vessel are not critical. Temperatures of from about 10° to about 95° C., and more generally from about 20° to about 80° C. may be used. Ambient temperature is common. Generally, the conditions are controlled to result in the preparation of a catalyst having the desired characteristics and properties.

The water-soluble copper, iron and manganese salts utilized to form the first solution may be salts such as nitrates, acetates, sulfates, chlorides, etc. It is presently preferred, however, to use the nitrates of copper, iron and manganese in the formation of the first solution. Any water-soluble salt can be utilized to prepare the second solution, and the aluminum salt generally is a basic aluminum salt such as sodium aluminate.

The atomic ratio of copper to iron in the first solution is at least 1:1 and generally from about 3:1 or from about 4:1 up to about 6:1. The amount of manganese contained in the first aqueous solution is an amount sufficient to provide a final catalyst containing from about 1% to about 15% by weight of manganese and in another embodiment, from about 1% to about 10% by weight of manganese. The amount of aluminum contained in the second solution should be an amount sufficient to provide a catalyst containing the desired amount of alumina. Generally, the amount of aluminum in the second solution is an amount which provides a copper to aluminum ratio in the final catalyst of from about 1:1 to about 3:1.

When it is desired to incorporate a small amount of a porous carrier material in the catalyst of the present invention, the carrier is suspended in water in the vessel to which the first and second solutions are added. In one embodiment, the carrier in the water is present as an alkaline earth metal silicate such as calcium silicate. The amount of alkaline earth metal silicate included in the vessel is an amount calculated to provide the desired amount of the carrier material in the finished catalyst. In one embodiment, the catalysts contain up to about 20% by weight, preferably containing up to about 15% by weight of the carrier, generally present as calcium silicate.

The second solution also contains at least one alkaline precipitating agent which may be a soluble base such as sodium hydroxide, sodium carbonate, ammonium hydroxide, ammonium carbonate, etc., and mixtures thereof. The amount of the soluble base included in the second solution may be varied over a wide range, and the amount of the soluble base should be sufficient to provide an alkaline solution which, when added to the reaction vessel, will result in a mixture having the desired pH. The pH of the mixture obtained by mixing the first and second solutions should be within the range of from about 5.5 to about 9.0, and more preferably, is at least 6. As noted above, the pH of the mixture can also be maintained as desired by adjusting the relative addition rates of the two solutions. Upon mixing the first and second solutions, a precipitate is formed and is recovered by techniques well known to those skilled in the an such as by sedimentation, filtration, centrifugation, etc.

The solids which are recovered may be washed with water to remove impurities and dried by heating to a temperature of up to about 150° C. The dried solids are then calcined at a desirable temperature such as temperatures in the range of from about 350° to about 700° C. The time of calcination can be varied over a wide range, and will depend, in part, on the amount of powder calcined and the temperature of calcination. Generally, calcination in a period of from about 10 to about 120 minutes. In one embodiment, calcination at a temperature of about 500° C. for about one hour is sufficient.

The following examples illustrate various embodiments of the present invention for preparing the powdered copper, iron, aluminum and manganese-containing catalysts. Unless otherwise indicated in the examples and elsewhere in the specification and claims, all parts and percentages are by weight, temperatures are in degrees Centigrade, and pressures at or near atmospheric.

EXAMPLE 1

A first solution containing 755 parts of copper nitrate solution (16.5% copper, 233 parts of iron nitrate (9.3% iron) and 137 parts of manganese nitrate (15.5% manganese) and 1000 parts of water is prepared. A second solution is prepared containing 498 parts sodium aluminate solution (10.5% aluminum), 182 parts of sodium carbonate and 1000 parts of water. The two solutions are then added slowly and simultaneously with agitation to a vessel containing 5000 parts of water at 70° C. The pH is maintained at about 6.5 by varying the addition rate of the first solution. The resulting precipitate is recovered by filtration, washed with water to remove residual salts and dried at 120° C. The dried material is crushed and calcined at 500° C. for one hour. Some of the characteristics of the calcined product are reported in Table I.

EXAMPLE 2

The procedure of Example 1 is repeated except that only about 55 parts of manganese nitrate is incorporated into the first solution. Some of the characteristics of the calcined product obtained in this manner are reported in Table I.

EXAMPLE 3

The procedure of Example 1 is repeated except that the first solution contains 220 parts of manganese nitrate. Some of the characteristics of the product obtained in this example are reported in Table I.

EXAMPLE 4

A first solution containing 755 parts of copper nitrate solution (16.5% copper), 233 parts of iron nitrate (9.3% iron), 137 parts of manganese nitrate (15.5% manganese) and 1000 parts of water is prepared. A second solution is prepared containing 498 parts of sodium aluminate solution (10.5% aluminum), 182 parts of sodium carbonate and 1000 parts of water. These two solutions are added slowly and simultaneously, with agitation, to a vessel containing 36 parts of calcium silicate suspended in 5000 parts of water at 70° C. The pH is maintained at about 6.5 by varying the addition rate of the first solution. The resulting precipitate is recovered by filtration, washed with water to remove residual salts, and dried at 120° C. The dried material was then crushed and calcined at 500° C. for one hour. Some of the characteristics of this calcined product are reported in Table I.

TABLE I

| Catalyst Characteristics | | | | |
|---|---|---|---|---|
| | Example | | | |
| | 1 | 2 | 3 | 4 |
| Surface Area | 86 | 80 | 131 | 155 |
| Hg Pore Vol. (% of Total @ 1000 Å) | | | | |
| up to 90 Å | 16.8 | 17.2 | 11.8 | 14.0 |
| up to 120 Å | 18.8 | 18.2 | 16.1 | 19.6 |
| up to 200 Å | 25.3 | 21.8 | 28.4 | 35.0 |
| up to 350 Å | 39.7 | 31.9 | 46.3 | 54.5 |
| up to 700 Å | 79.6 | 71.7 | 80.4 | 83.3 |
| up to 1000 Å | 100 | 100 | 100 | 100 |
| P. V. @ 1000 Å | 0.84 | 0.95 | 0.91 | 1.07 |
| Chemical Data | | | | |
| Copper | 44.4 | 42.1 | 39.7 | 34.4 |
| Manganese | 2.9 | 7.6 | 10.9 | 5.2 |
| Iron | 7.5 | 6.9 | 6.7 | 6.5 |
| Aluminum | 13.5 | 12.1 | 11.1 | 13.2 |
| Calcium | — | — | — | 4.1 |
| Silicon | — | — | — | 2.9 |

The catalysts of the present invention which contain copper, iron, alumina and manganese have been found to be particularly useful for hydrogenating aldehydes, ketones, carboxylic acids and carboxylic esters to alcohols.

The catalysts of the present invention which are prepared as powders may be utilized in slurry- (liquid-) phase hydrogenation processes. Alternatively, the powders can be processed into shapes such as pellets and used in fixed bed reactors. In one embodiment, carboxylic acids and carboxylic esters can be converted to alcohols in excellent yields using the catalyst of the present invention. The esters may be monoesters or diesters. Among the carboxylic acids which may be hydrogenated to the corresponding alcohols are stearic acids and caproic acids. Preferably, the esters of such acids and their corresponding alcohols are converted to alcohols using the catalysts of this invention. For example, stearyl stearate is convened to stearic alcohol. Esters derived from the alcohols of higher molecular weight carboxylic acids are hydrogenated more rapidly and at lower temperatures than the esters derived from the lighter alcohols. Examples of carboxylic acids which may be hydrogenated with the catalyst of the present invention include coconut fatty acid, stearic acid, oleic acid, lauric acid, myristic acid and esters such as the diethyl ester of ethyl malonic acid, diethyl succinate, di-n-butyl glutarate, diethyl sebacate. As noted, the esters are converted to alcohols, and examples of such conversions include: lauryl laurate to lauryl alcohol; myristyl myristate to myristyl alcohol; amyl valerate to n-amyl alcohol; methyl caproate to n-hexyl alcohol, etc.

Examples of aldehydes which may be hydrogenated with the catalyst of the present invention include: butyraldehyde, furfural, 2-ethyl-hexanal, dodecanal, tetradecanal, etc. Examples of ketones include acetone, acetophenone, etc.

The hydrogenation reactions which are conducted in the presence of the catalyst of the present invention are carried out at temperatures of from about 250° C. to about 350° C. and at pressures of from about 1500 psi to about 4500 psi.

The hydrogenation activity of the catalyst of Examples 1–4 is demonstrated by carrying out hydrogenation reactions of coconut fatty acid at 300° C., 4350 psig of hydrogen and 0.75 weight percent catalyst loading. The effectiveness of the catalyst is determined by measuring the saponification value for each of the samples pursuant to A.O.C.S. official method Cd 3-25, revised April, 1966, reapproved 1973. Under these specific test conditions, saponification values of below about 50 indicate good hydrogenation activity. The results of this test are shown in Table II, and the results demonstrate excellent hydrogenation activity.

TABLE II

| Catalyst of Example | Catalytic Activity Saponification Value |
| --- | --- |
| 1 | 16.7 |
| 2 | 11.6 |
| 3 | 12.8 |
| 4 | 12.3 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A catalyst in powdered form consisting essentially of the oxides of copper, iron, aluminum and manganese wherein the atomic ratio of copper to iron is at least 1:1; wherein said catalyst contains at least about 1% by weight each of manganese and aluminum and the atomic ratio of copper to aluminum is at least about 1:1.

2. The catalyst of claim 1 wherein the powders have a surface area of at least about 50 m$^2$/g.

3. The catalyst of claim 1 wherein the powders have a surface area of from about 50 to about 175 m$^2$/g.

4. The catalyst of claim 1 wherein the atomic ratio of copper to iron is from about 3:1 to about 6:1.

5. The catalyst of claim 1 containing from about 1 to about 15% by weight of manganese.

6. The catalyst of claim 1 wherein the atomic ratio of copper to aluminum is from about 1:1 to about 3:1.

7. The catalyst of claim 1 which also contains a minor amount of at least one inorganic carrier material.

8. The catalyst of claim 7 containing up to about 20% of the carrier material.

9. The catalyst of claim 7 wherein the carrier is calcium silicate.

10. The catalyst of claim 1 which is free of chromium.

11. The catalyst of claim 1 wherein the atomic ratio of copper to manganese is from about 2:1 to about 35:1.

12. A catalyst in powdered form consisting essentially of the oxides of copper, iron, aluminum and manganese wherein the atomic ratio of copper to iron is from about 4:1 to about 6:1, the atomic ratio of copper to aluminum is from about 1:1 to about 3:1, and the catalyst contains from about 1 to about 10% by weight of manganese and from about 1 to about 10% by weight aluminum.

13. The catalyst of claim 12 also containing up to about 15% by weight of a porous inorganic carrier material.

14. The catalyst of claim 13 wherein the carrier is present as calcium silicate.

15. The catalyst of claim 12 wherein the powders have a surface area in the range of from about 70 to about 160 m$^2$/g.

16. A process for preparing a hydrogenation catalyst consisting essentially of the oxides of copper, iron, aluminum and manganese which comprises the steps of (A) preparing a first aqueous solution containing at least one water-soluble copper salt, at least one water-soluble iron salt, and at least one water-soluble manganese salt wherein the atomic ratio of copper to iron in the first aqueous solution is at least 1:1, the amount of manganese contained in the first aqueous solution is an amount sufficient to provide a final catalyst containing at least about 1% by weight of manganese and the atomic ratio of copper to aluminum is at least about 1:1;

(B) preparing a second solution containing at least one water-soluble basic aluminum salt and at least one alkaline precipitating agent, the amount of aluminum contained in the second solution is an amount sufficient to provide a catalyst containing at least about 1% aluminum;

(C) mixing the first and second solutions whereby an insoluble solid is formed;

(D) recovering the insoluble solid; and (E) calcining the recovered solid to produce said catalyst in oxide form.

17. The process of claim 16 wherein the atomic ratio of copper to iron in the first aqueous solution is within the range of from about 3:1 to about 6:1.

18. The process of claim 16 wherein the atomic ratio of copper to manganese in the first aqueous solution is from about 2:1 to about 35:1.

19. The process of claim 16 wherein the catalyst recovered from the calcination in step (E) contains from about 1 to about 15% by weight of manganese.

20. The process of claim 16 wherein the first and second solutions are simultaneously mixed in step (C).

21. The process of claim 16 wherein the first and second solutions are simultaneously added with mixing to a vessel containing water and at least one alkaline earth metal silicate.

22. A process for preparing a hydrogenation catalyst consisting essentially of the oxides of copper, iron, aluminum and manganese which comprises the steps of (A) preparing a first aqueous solution containing at least one water-soluble copper salt, at least one water-soluble iron salt, and at least one water-soluble manganese salt in an amount sufficient to provide an atomic ratio of copper to iron of from about 3:1 to about 6:1, and an atomic ratio of copper to manganese of from about 2:1 to about 20:1, the amount of manganese contained in the first aqueous solution is an amount sufficient to provide a final catalyst containing at least about 1% by weight of manganese;

(B) preparing a second solution containing at least one water-soluble basic aluminum salt and at least one alkaline precipitating agent, the amount of aluminum contained in the second solution is an amount sufficient to provide a catalyst containing at least about 1% by weight aluminum;

(C) simultaneously mixing the first and second solutions in a vessel containing water and calcium silicate whereby an insoluble solid is formed;

(D) recovering the insoluble solids; and (E) calcining the recovered solid to produce said catalyst in oxide form.

23. The process of claim 22 wherein the catalyst recovered from the calcination in step (E) contains from about 1 to about 15% by weight of manganese.

* * * * *